United States Patent
Avallin et al.

(10) Patent No.: US 12,280,168 B2
(45) Date of Patent: Apr. 22, 2025

(54) METHOD FOR SANITIZATION OF A CHROMATOGRAPHY COLUMN

(71) Applicant: Cytiva Sweden AB, Uppsala (SE)

(72) Inventors: Johan Avallin, Uppsala (SE); Anna Gronberg, Uppsala (SE); Anders Nilsson, Uppsala (SE); Henrik Ingvarsson, Uppsala (SE); Linda Persson, Uppsala (SE); Magnus Asplund, Uppsala (SE); Reinhard Braaz, Penzberg (DE)

(73) Assignee: Cytiva Sweden AB, Uppsala (SE)

( * ) Notice: Subject to any disclaimer, the term of this patent is extended or adjusted under 35 U.S.C. 154(b) by 733 days.

(21) Appl. No.: 17/437,097

(22) PCT Filed: Mar. 23, 2020

(86) PCT No.: PCT/EP2020/058023
§ 371 (c)(1),
(2) Date: Sep. 8, 2021

(87) PCT Pub. No.: WO2020/193485
PCT Pub. Date: Oct. 1, 2020

(65) Prior Publication Data
US 2022/0175992 A1    Jun. 9, 2022

(30) Foreign Application Priority Data
Mar. 26, 2019    (GB) ...................................... 1904125

(51) Int. Cl.
*A61L 2/18*    (2006.01)
*B01D 15/20*    (2006.01)
(Continued)

(52) U.S. Cl.
CPC ............ *A61L 2/186* (2013.01); *B01D 15/203* (2013.01); *B01D 15/3809* (2013.01);
(Continued)

(58) Field of Classification Search
CPC .. B01D 15/203; B01D 15/3809; G01N 30/50; G01N 30/56; G01N 30/6021; G01N 30/6026; A61L 2101/36; A61L 2202/23
See application file for complete search history.

(56) References Cited

U.S. PATENT DOCUMENTS

| | | |
|---|---|---|
| 5,902,485 A | 5/1999 | Davis et al. |
| 2003/0098280 A1 | 5/2003 | Davis et al. |

(Continued)

FOREIGN PATENT DOCUMENTS

| | | |
|---|---|---|
| JP | 10-503470 A | 3/1998 |
| JP | 2016-507729 A | 3/2016 |

(Continued)

OTHER PUBLICATIONS

PCT International Search Report and Written Opinion for PCT/EP2020/058023 mailed May 26, 2020 (9 pages).

(Continued)

*Primary Examiner* — Timothy C Cleveland
(74) *Attorney, Agent, or Firm* — Eversheds-Sutherland (US) LLP

(57) ABSTRACT

The invention discloses a method for sanitization of a bioprocess chromatography column, comprising the steps of: a) providing a bioprocess chromatography column with a packed bed of separation resin particles and a movable adapter, b) with the adapter in contact with the packed bed, conveying a sanitization fluid through the packed bed to a column outlet; c) raising the adapter to provide a gap between the packed bed and the adapter, d) lowering the adapter to close the gap; and e) conveying an equilibration liquid through the packed bed to a column outlet.

18 Claims, 12 Drawing Sheets

(51) Int. Cl.
    *B01D 15/38*     (2006.01)
    *G01N 30/50*     (2006.01)
    *G01N 30/56*     (2006.01)
    *G01N 30/60*     (2006.01)
    *A61L 101/36*     (2006.01)

(52) U.S. Cl.
    CPC .............. *G01N 30/50* (2013.01); *G01N 30/56* (2013.01); *G01N 30/6021* (2013.01); *G01N 30/6026* (2013.01); *A61L 2101/36* (2020.08); *A61L 2202/23* (2013.01)

(56) References Cited

U.S. PATENT DOCUMENTS

| | | |
|---|---|---|
| 2013/0248430 A1 | 9/2013 | Gu |
| 2015/0328563 A1 | 11/2015 | Lacki et al. |
| 2018/0036445 A1 | 2/2018 | Monie et al. |

FOREIGN PATENT DOCUMENTS

| | | |
|---|---|---|
| JP | 2017-146239 A | 8/2017 |
| JP | 2018-044921 A | 3/2018 |
| WO | 95/26711 A1 | 10/1995 |
| WO | 14/092636 A1 | 6/2014 |
| WO | 2016/139128 A1 | 9/2016 |
| WO | 2015/118609 A | 3/2017 |

OTHER PUBLICATIONS

Great Britain Search Report for GB Application No. 11904125.0 mailed Sep. 25, 2019 (5 pages).

Japanese Office Action for JP 2021-557165, mailed Jan. 15, 2024 (9 pages).

Korean Office Action issued in corresponding KR Application No. 10-2021-7029926, mailed Feb. 7, 2025, 19 pages.

| 301 | Fill column with slurry |
| 304 | Consolidate the bed |
| 306 | Lower the adapter to final bed height |
| 308 | Rinse with water |
| 310 | Treat with sanitization fluid |
| 312 | Raise the adapter and treat with sanitization fluid |
| 314 | Lower the adaptor |
| 316 | Treat with sanitization fluid |
| 318 | Equilibrate with equilibration liquid (e.g. water) |

…

METHOD FOR SANITIZATION OF A CHROMATOGRAPHY COLUMN

CROSS REFERENCE TO RELATED APPLICATIONS

This application claims the priority benefit of PCT/EP2020/058023, filed on Mar. 23, 2020, which claims the benefit of Great Britain Application No. 1904125.0, filed Mar. 26, 2019, the entire contents of which are incorporated by reference herein.

TECHNICAL FIELD OF THE INVENTION

The present invention relates to bioprocess chromatography columns, and more particularly to a method for sanitization of a bioprocess chromatography column with a sanitization fluid.

BACKGROUND OF THE INVENTION

Microbial contaminations are found in many laboratory and production environments. Growing rapidly to large quantities under favorable conditions, these microorganisms can damage the function and impair the performance of chromatographic equipment and chromatography resins. Additionally, microorganisms can remain as contaminants of the bioproduct throughout manufacturing, with batch failure and related costs as consequence. Consequently, it is important to follow hygienic routines throughout the whole production process. Sanitization, defined as the use of chemical agents to reduce microbial populations, is commonly used for chromatography systems to maintain microbial presence at levels that minimize the risk of contaminating the bioproduct.

The sanitization agent peracetic acid (PAA) is an oxidizing agent efficient for removal of both vegetative and spore-forming bacteria, as discussed in US20180036445, hereby incorporated by reference in its entirety. The agent is compatible with e.g. Protein A resins and most hardware bioprocess equipment. It has been shown that treatment of a Protein A resin with 20 mM aqueous PAA for 30 min or 30 mM PAA for 15 min can be used without significantly affecting purification performance of the resin. It is also known that NaOH solutions can be used for sanitization of chromatography resins—see WO2017194593A1, hereby incorporated by reference in its entirety.

For a sanitization of a packed bed column to be effective, it is essential that the entire bed and all liquid-contact surfaces are contacted by the sanitization agent. This is particularly important for modern process columns with a movable adapter, where a stagnant zone is present between the top bed support and the column tube.

Accordingly, there is a need for a packed bed column sanitization method allowing efficient contact between a sanitization agent and the entire resin amount in the bed, as well as with all liquid-contact column surfaces.

SUMMARY OF THE INVENTION

One aspect of the invention is to provide a method for sanitization of a bioprocess chromatography column. This is achieved with a method comprising the steps of:
a) providing a bioprocess chromatography column with a packed bed of separation resin particles and a movable adapter;
b) with the adapter in contact with the packed bed, conveying a sanitization fluid through the packed bed to a column outlet;
c) raising the adapter to provide a gap between the packed bed and the adapter;
d) lowering the adapter to close the gap; and
e) conveying an equilibration liquid through the packed bed to a column outlet.

One advantage is that an efficient sanitization of the bed can be obtained in situ, without any need for repacking the bed. A further advantage is that the method is amenable for automation.

Further suitable embodiments of the invention are described in the dependent claims.

DRAWINGS

DEFINITIONS

To more clearly and concisely describe and point out the subject matter of the claimed invention, the following definitions are provided for specific terms that are used in the following description and the claims appended hereto.

The singular forms "a" "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least each numerical parameter should at least be construed in light of the number of reported significant digits and by applying ordinary rounding techniques.

As used herein to describe the present invention, directional terms such as "up", down", "upwards", "downwards", "upper", "lower", "top", "bottom", "vertical", "horizontal", "above", "below" as well as any other directional terms, refer to those directions in the appended drawings.

DETAILED DESCRIPTION OF EMBODIMENTS

Figure 1:
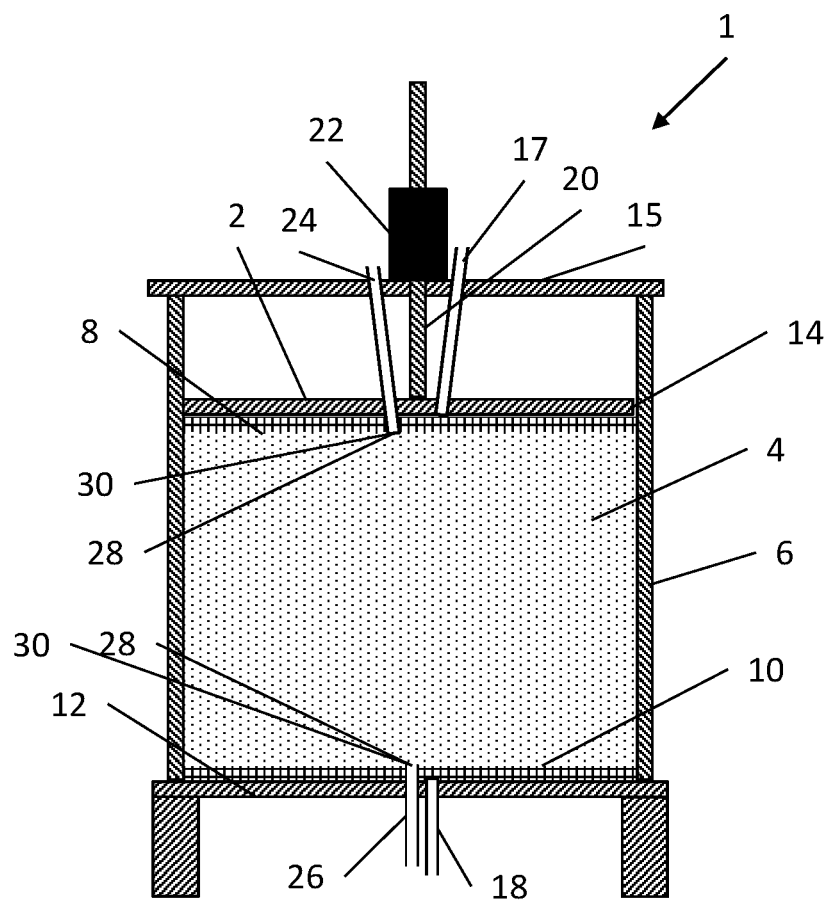
FIG. 1 shows a schematic overview of a bioprocess column with a movable adapter.
Figure 2:
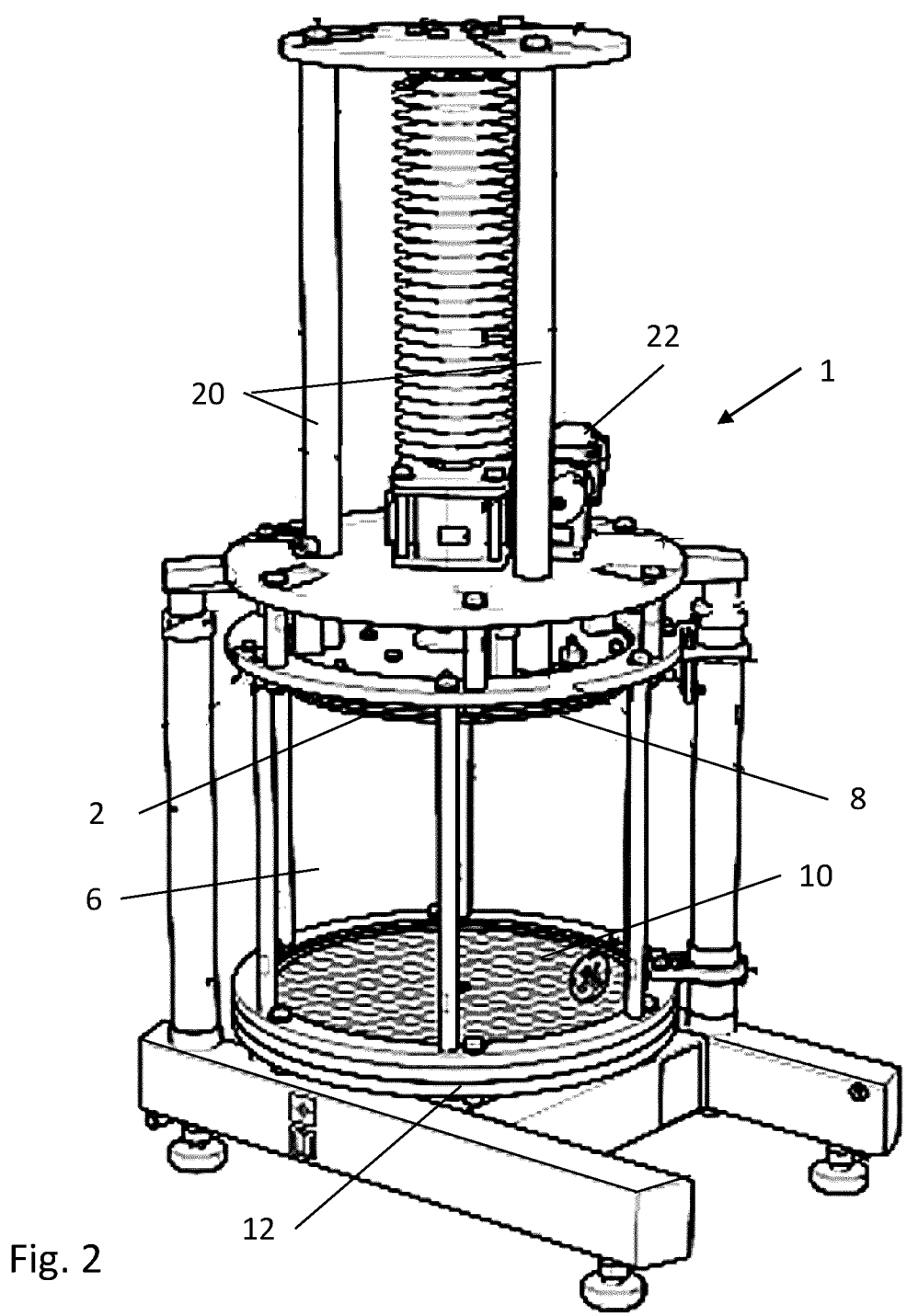
FIG. 2 shows a perspective view of a bioprocess column with a movable adapter.
Figure 3:
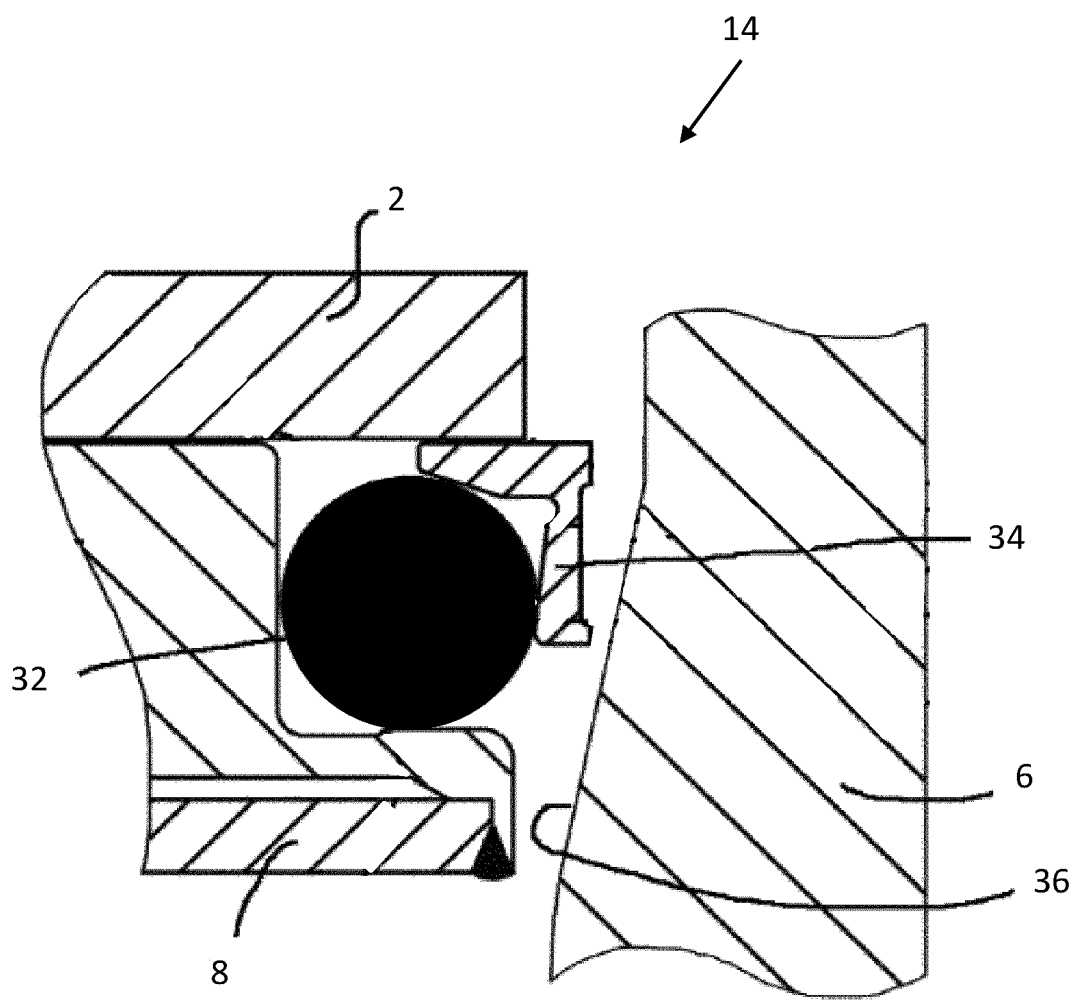
FIG. 3 shows a slidable seal between a movable adapter and a column wall.
Figure 4:
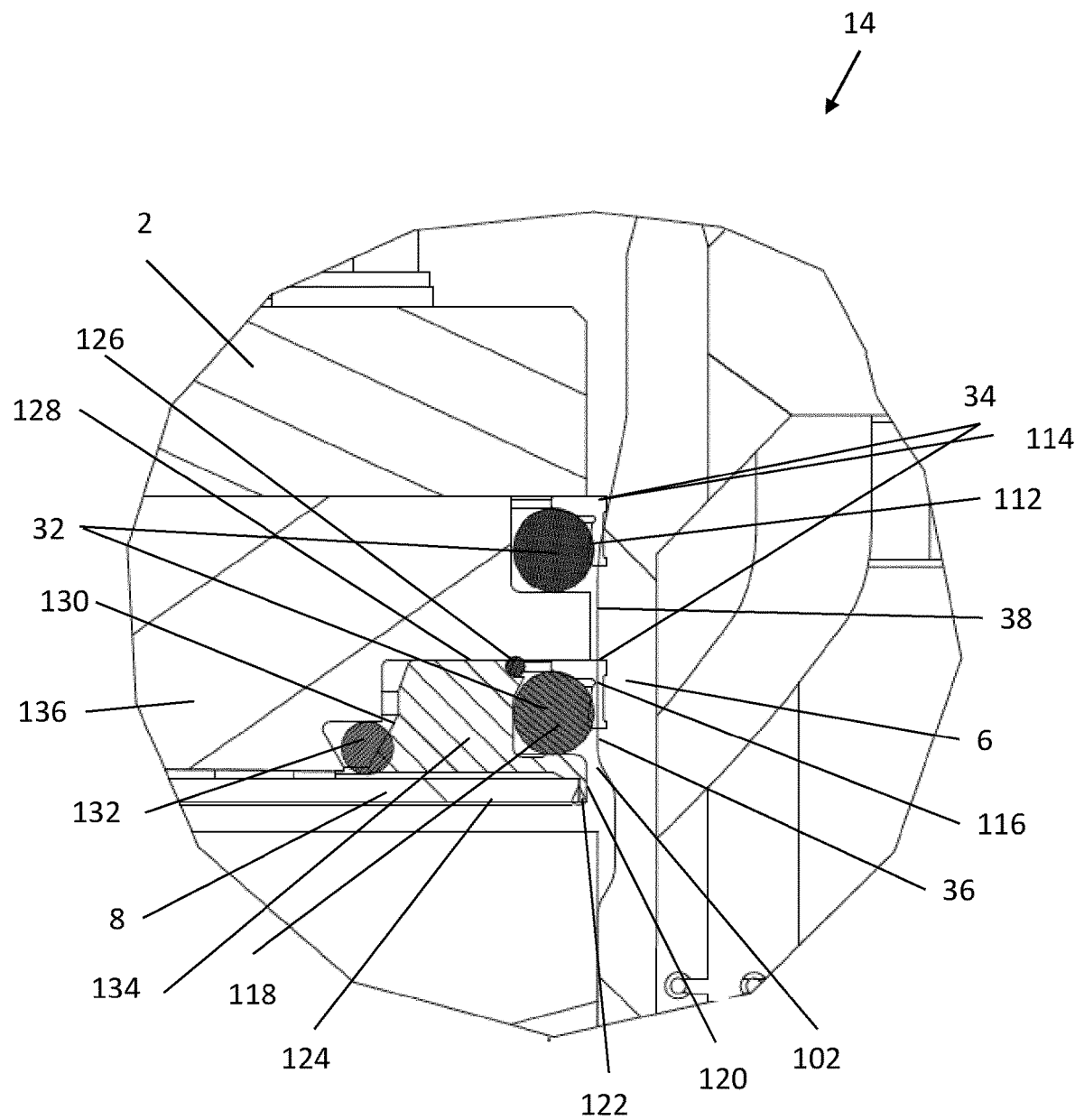
FIG. 4 shows an alternative arrangement of the adapter-column wall sealing.
Figure 5:
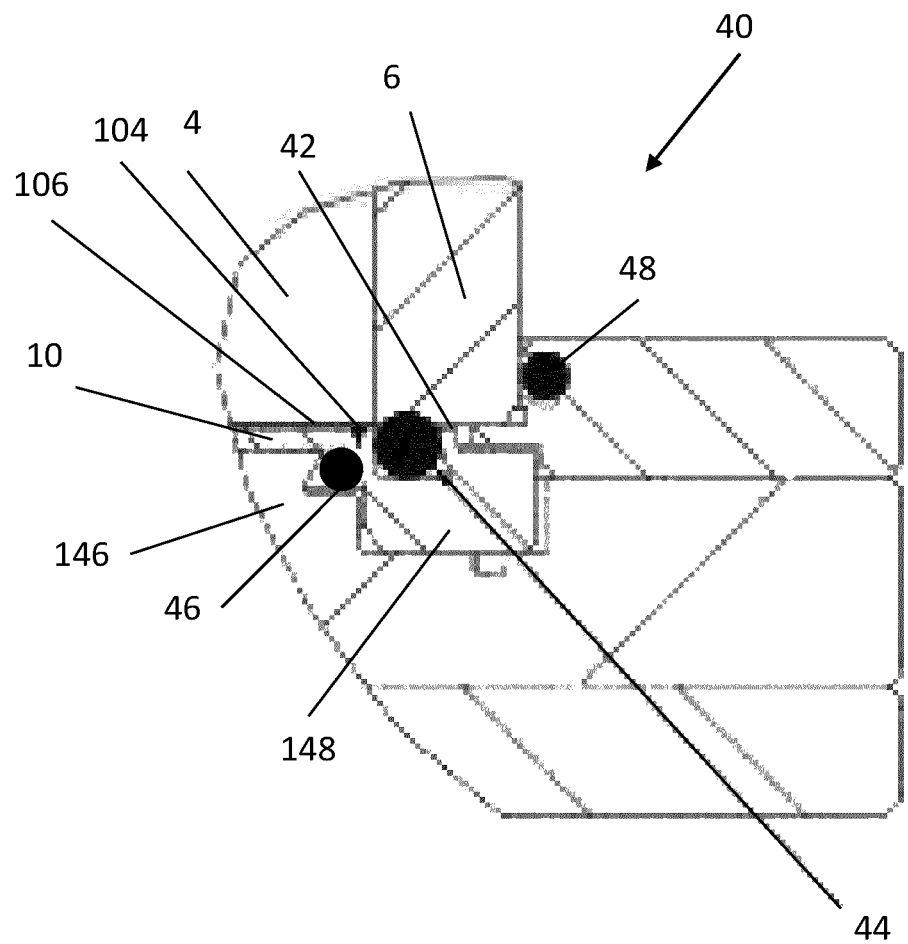
FIG. 5 shows a seal between a bottom bed support and a column wall.
Figure 6:
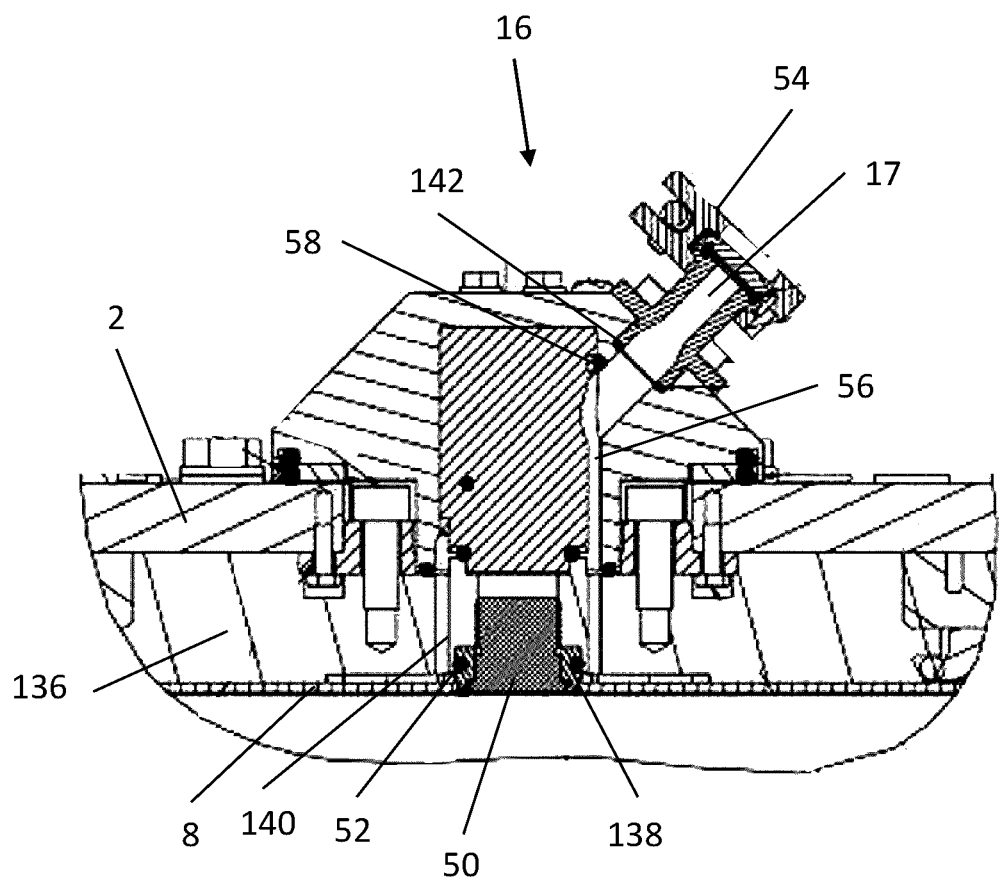
FIG. 6 shows a top valve assembly with mobile phase inlet/outlet in an adapter.
Figure 7:
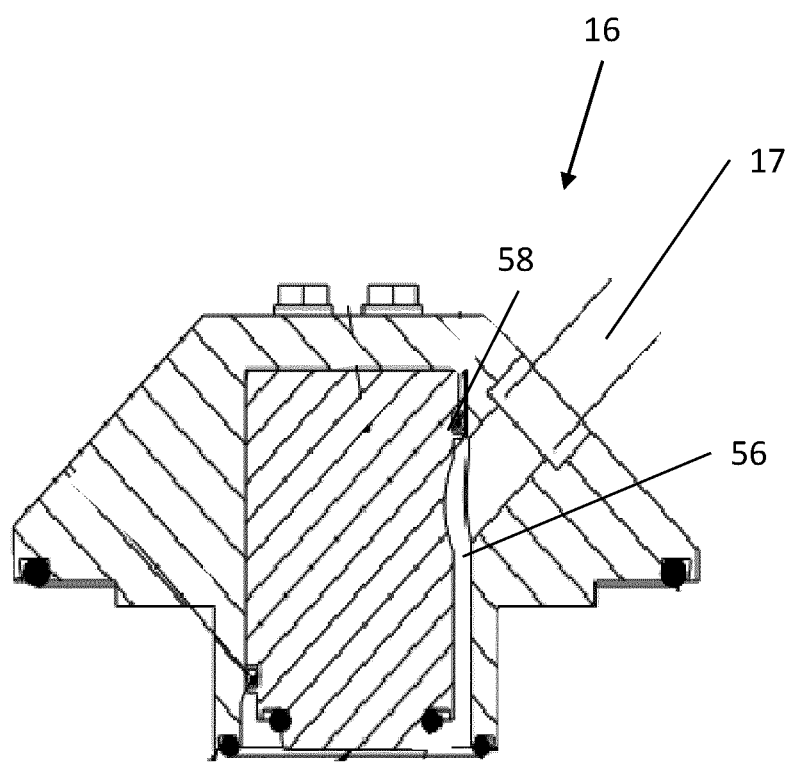
FIG. 7 shows a top valve subassembly with mobile phase inlet/outlet in an adapter.
Figure 8:
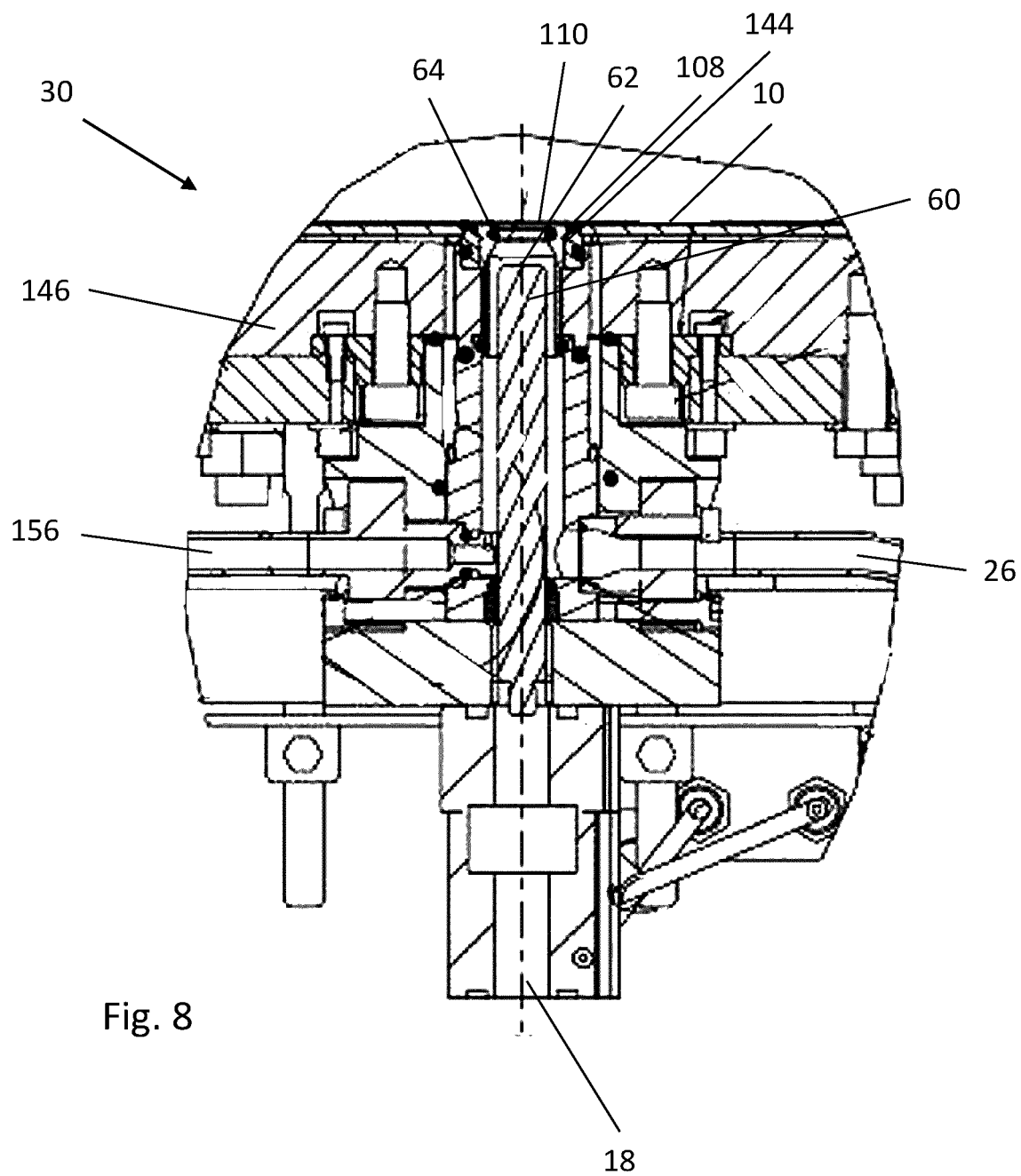
FIG. 8 shows an integrated mobile phase and resin valve in a bottom bed support.
Figure 9:
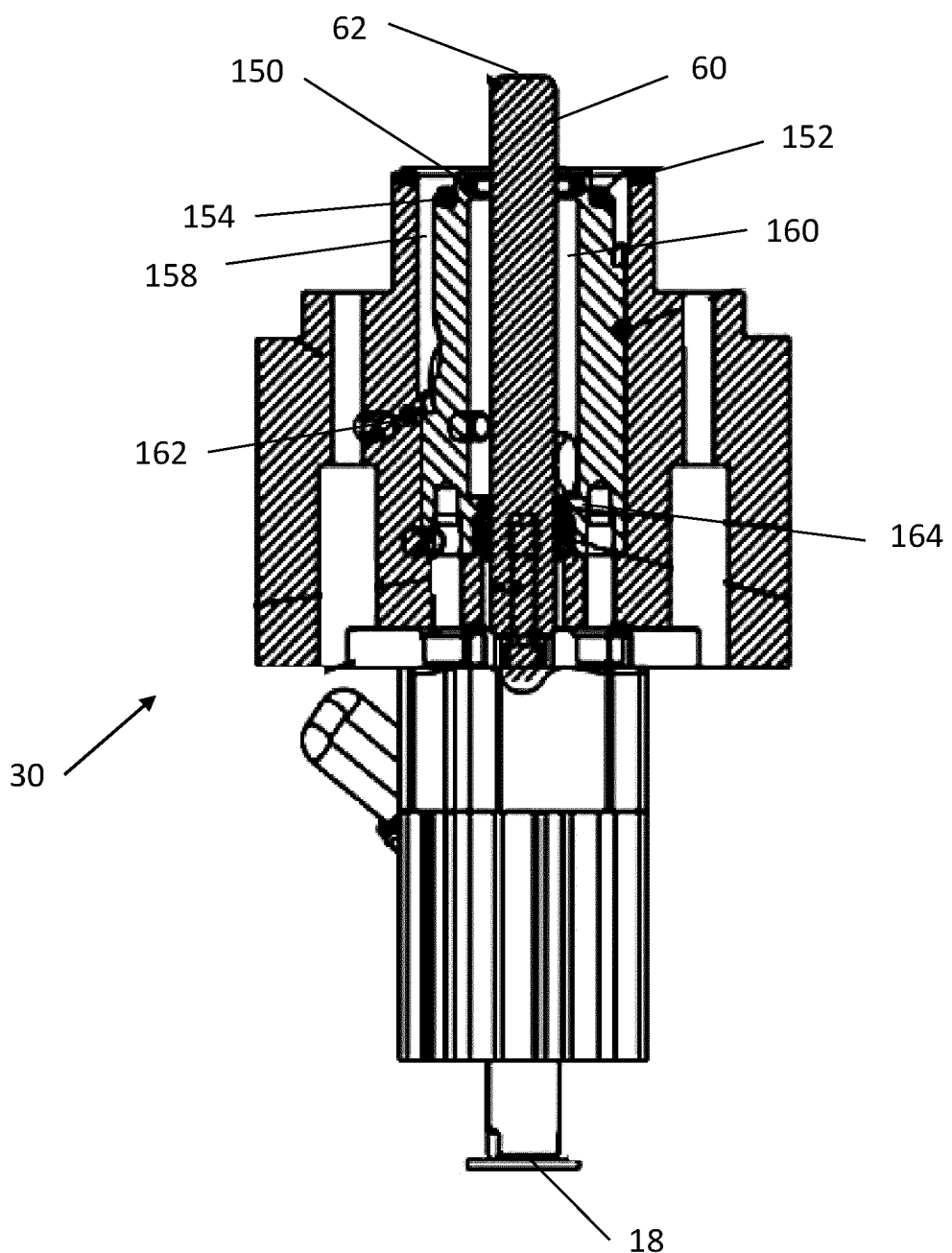
FIG. 9 shows an integrated mobile phase and resin valve in a bottom bed support.
Figure 10:
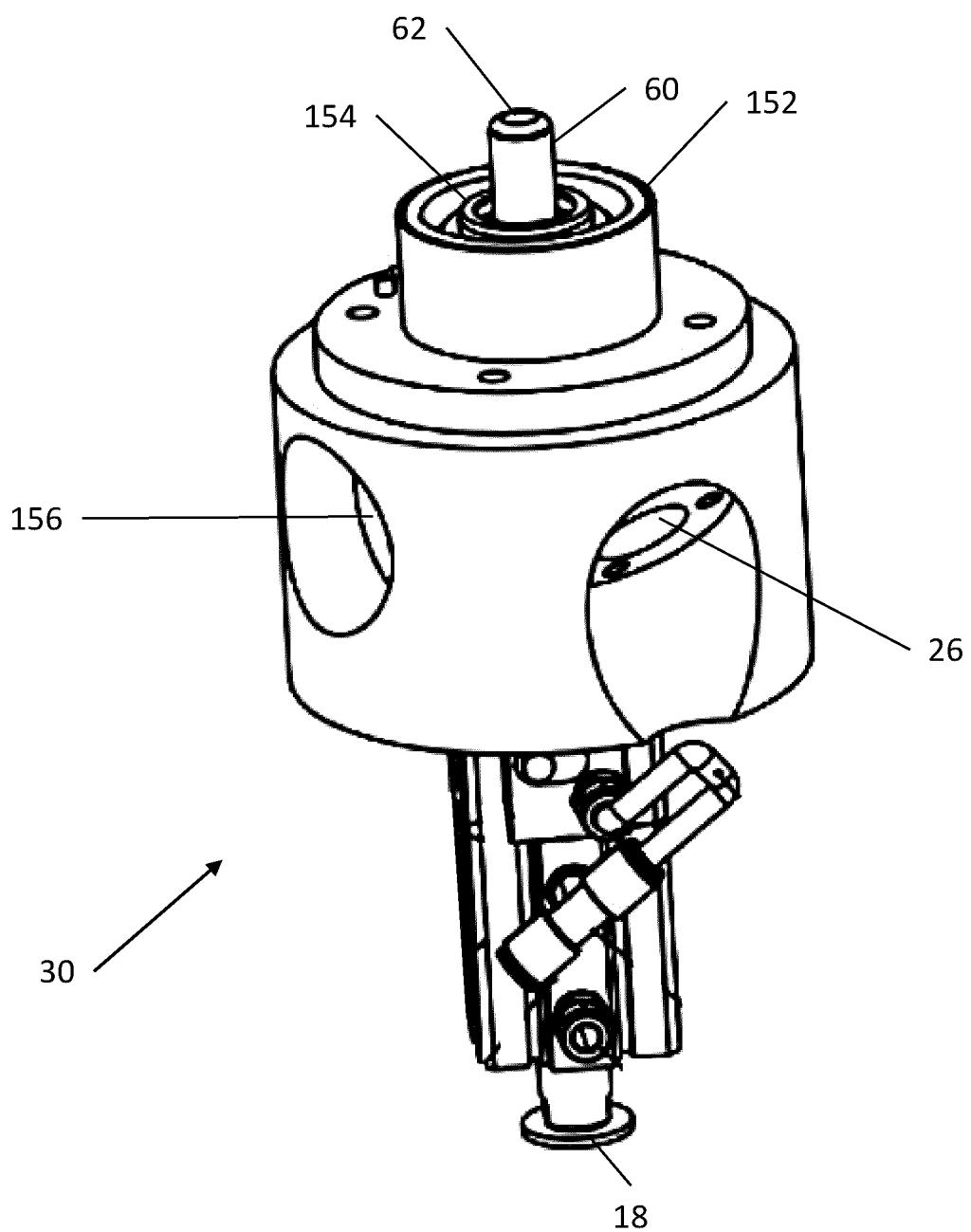
FIG. 10 shows an integrated mobile phase and resin valve in a bottom bed support.
Figure 11:
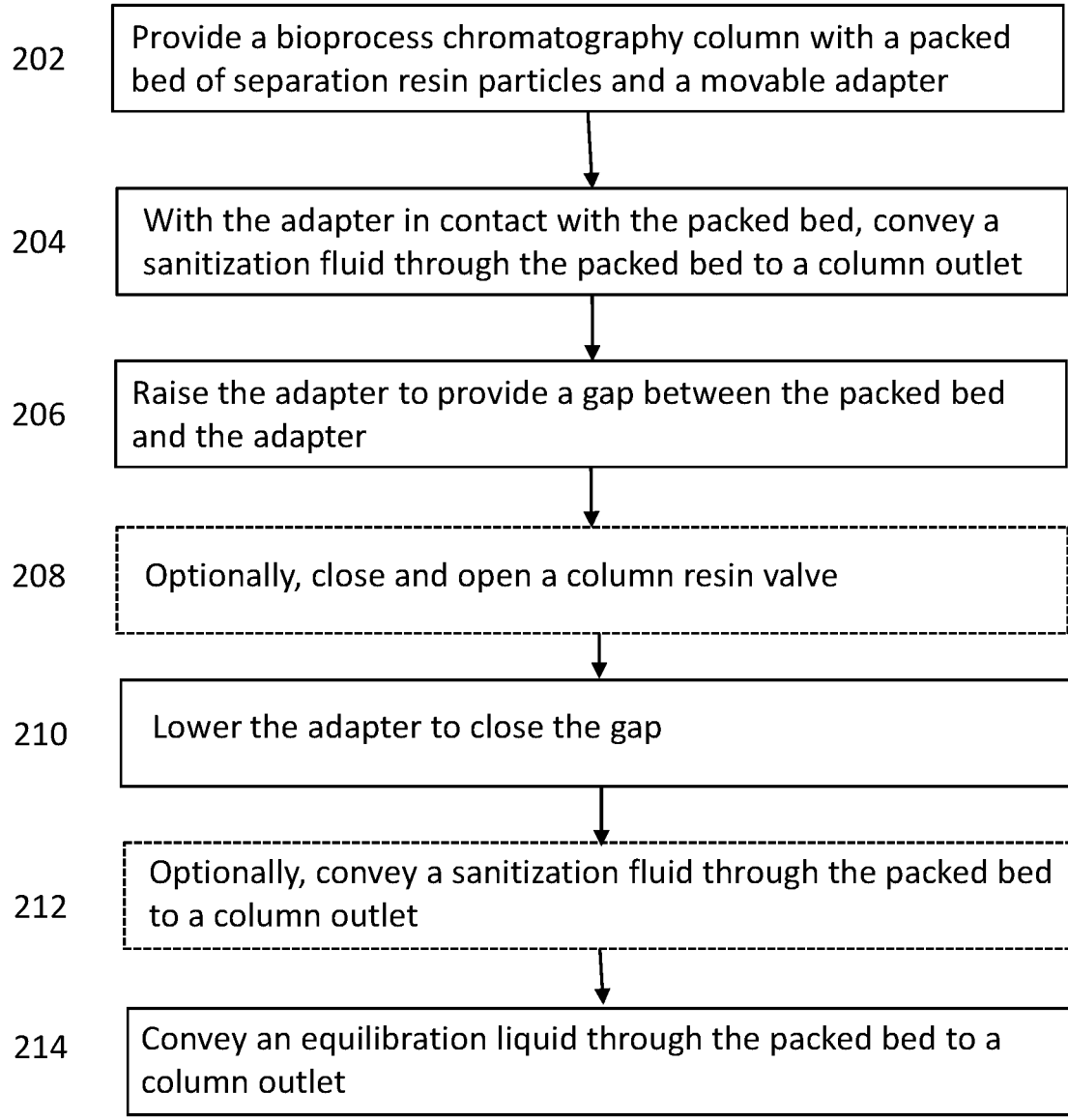
FIG. 11 shows a schematic view of a sanitization process.

In one aspect, illustrated by FIGS. 1-12, the present invention discloses a method for sanitization of a bioprocess chromatography column. The method comprises the steps of:

a) Providing a bioprocess chromatography column 1 with a packed bed 4 of separation resin particles and a movable adapter 2. The adapter can be vertically movable by means of e.g. one or more electrical motors 22 or hydraulic actuators. The separation resin may comprise a crosslinked polysaccharide, such as crosslinked agarose. Alternatively, it may comprise a synthetic crosslinked polymer, e.g. a styrene-divinylbenzene copolymer or a methacrylate copolymer. The resin may comprise ligands such as affinity ligands, ion exchange ligands, multimodal ligands and/or hydrophobic ligands. In particular, proteinaceous affinity ligands may be tethered to the separation resin. These proteinaceous affinity ligands may e.g. comprise Protein A or a variant of Protein A. Examples of Protein A variants include alkali-stable Protein A-derived ligands as disclosed in e.g. US20170334954, U.S. Pat. No. 7,834,158, US2018094024, U.S. Pat. Nos. 8,329,860, 9,018,305, US2013046056, U.S. Pat. Nos. 9,040,661, 9,403,883, US20160237124, US2018105560, US2014031522, US2010286373, CN105481954A, US20160159855, US20160159857 and WO2018029158, all of which are hereby incorporated by reference in their entireties. Commercially available separation resins having such Protein A variant ligands include e.g. MabSelect™ SuRe (GE Healthcare, MabSelect PrismA (GE Healthcare), Eshmuno™ A (EMD-Millipore), Amsphere™ A3 (JSR), TOYOPEARL™ AF-rProtein A (Tosoh Bioscience), KanCapA™ (Kaneka) and Praesto™ Jetted A50 (Purolite). The column may be a commercially available bioprocess column with movable adapter, such as e.g. AxiChrom™ (GE Healthcare), Resolute™ (Pall), Prochrom™ (Novasep), EAC-Bio (Lisure Science), Easy-Pack™ (Verdot) etc. The column (packed bed) diameter may e.g. be 5 cm-2 m, such as 10 cm-2 m or even 30 cm-2 m, and the bed height may e.g. be 5 cm-50 cm, such as 8-30 cm. A typical construction of a column 1 with movable adapter 2 is schematically shown in FIG. 1 and as a perspective drawing of an actual commercial column in FIG. 2. A packed bed of separation resin 4 is contained in a cylindrical column tube 6 between upper 8 and lower 10 porous bed supports. The lower bed support rests on a liquid distributor 146, supported by a column bottom 12. The upper bed support is connected via a liquid distributor 136 to a movable adapter 2, which is slidably sealed to the column tube by sealing 14. An example of sealing 14 is showed enlarged in FIG. 3. In this case, an O-ring 32 urges a scraper ring 34 towards the inside 36 of the column tube 6. FIG. 4 shows another example of sealing 14, with two scraper rings 34,114,116 urged by O-rings 32,112,118 towards the inside of column tube 6. In this case there can also be a wash channel (not shown) in fluidic connection with the space 38 between the two scraper rings 34, allowing flushing of this space. FIG. 5 shows an enlarged example of a sealing 40 between the bottom end 42 of the column tube 6 and the lower bed support 10. This can be accomplished by O-rings 44, 46 and 48. The column tube may be covered by a fixed column lid 15. An upper mobile phase inlet/outlet 17, which may form part of an upper valve assembly 16, is fluidically connected, via the distributor, to the upper bed support and a lower mobile phase outlet/inlet 18 is fluidically connected, via the distributor, to the lower bed support, allowing mobile phase to be passed through the inlets/outlets and the packed bed in either upwards or downwards direction. The adapter may be connected to one or more adapter rods 20 for vertical (axial) movement. The adapter rod(s) can be connected to one or more actuators 22 configured to move the rod(s) vertically/axially. The actuator(s) can e.g. be one or more electrical motors or hydraulic cylinders. Alternatively, the adapter may be moved by motor-driven or manual screw action on threaded rod(s) or by hydraulic pressure applied directly on the top or bottom of the adapter. The column may further be equipped with one or more resin inlets/outlets 24,26 for packing and unpacking of the column. The resin inlets/outlets can be connected to the interior of the column, e.g. through the upper and/or lower bed supports and may have nozzles 28 for resin distribution and resin valves 30 for closure of the inlets/outlets during normal column operation. The resin and mobile phase inlets/outlets may be integrated with each other, such that when a resin valve is closed, flow goes from a mobile phase inlet via the distributor and bed support into the packed bed, and when the resin valve is open, flow goes from a resin inlet via a nozzle directly into the column tube. Examples of such valve and nozzle constructions are given in U.S. Pat. No. 5,902,485, which is hereby incorporated by reference in its entirety. FIG. 6 and FIG. 7 show an example of an upper valve assembly 16 having a mobile phase inlet/outlet 17, with details of a central screw 50 (sealed with O-ring 52) for fixation of the upper bed support 8. In this case, the inlet/outlet can be connected to tubing via a TC connector 54 and the liquid flows via an inlet/outlet chamber 56, sealed with an O ring 58. FIGS. 8-10 show a lower mobile phase outlet/inlet 18 integrated with a resin inlet/outlet 26 and a resin valve 30. Here, the resin valve 30 comprises a piston 60, which when the piston tip 62 is flush with the lower bed support 10 seals against O-ring 64 and directs mobile phase through the distributor and the lower bed support.

b) With the adapter in contact with the packed bed, conveying a sanitization fluid through the packed bed to a column outlet. The sanitization fluid can suitably comprise an oxidizing agent, such as a peracid (also called a peroxy acid) or hydrogen peroxide. In particular, the sanitization fluid may comprise peracetic acid. The concentration of the oxidizing agent (e.g. peracetic acid) can e.g. be 5-100 mM, such as 5-50 mM or 10-30 mM. Alternatively, the sanitization fluid may comprise an alkali metal hydroxide, e.g. NaOH. In this case, the concentration of the hydroxide may be 0.1-2 M, with preference for 0.5-2 M or 1-2 M. The contact time, i.e. the time the packed bed of separation resin is in contact with the sanitization fluid may e.g. be 10 min-2 h, such as 10-50 minutes or 20-40 minutes. Suitably, the temperature may be room temperature or 22+/−5° C. The density of the sanitization fluid may e.g. be 0.9-1.1 g/ml, such as 1.0-1.1 g/ml, and the viscosity of the fluid may e.g. be 1.0-2.0 mPas as measured at 22° C.

c) Raising the adapter to provide a gap between the packed bed and the adapter. The height of the gap may e.g. be 1 cm-10 cm, such as 2 cm-5 cm. Alternatively, it can be measured relative to the bed height and may e.g. be 10-40% of the bed height, such as 15-30% of the bed height. Raising the adapter allows improved contact between the sanitizing fluid and the deadlegs around the slidable sealing between the adapter and the column wall. In particular, it allows any trapped resin particles to sediment into the packed bed.

d) Lowering the adapter to close the gap. The adapter can suitably be lowered to the same position as it had in step b) or even to a somewhat lower position, e.g. to increase the compression with up to 0.04%, such as 0.02-0.03%. The compression increase provides an improved column efficiency.

e) Conveying one or more equilibration liquids through the packed bed to a column outlet. The equilibration liquid can e.g. be a bacteriostat solution, e.g. 20% aqueous ethanol, suitable for storage of the column. If the column is going to be used immediately afterwards for separations, the equilibration liquid can be water or an aqueous buffer, such as an equilibration buffer suitable for the intended chromatography step.

If the adapter has a flush channel between to slidable sealings, the method may further comprise filling this flush channel with sanitization fluid. As this sanitization fluid (which may be called a flush channel sanitization fluid) does not come into contact with the potentially sensitive separation resin, it can suitably contain a higher concentration of oxidizing agent such as peracetic acid, e.g. 50-150 mM or 70-120 mM peracetic acid. Filling the flush channel with sanitization fluid can suitably be done before step c), so that the column wall is sanitized during movement of the adapter. Before or after step e), the flush channel is then suitably washed with equilibration liquid.

In certain embodiments, the method further comprises, between steps d) and e), a step d') of conveying a sanitization fluid as discussed above through the packed bed to a column outlet.

In some embodiments, steps c) and d) are repeated at least once, such as twice. This further improves the contact between the sanitizing fluid and the adapter sealing deadlegs.

In certain embodiments, the method further comprises, after step b) and before step e), a step b') of closing and opening (or opening and closing) a column resin valve. This can further ensure that the sanitizing liquid penetrates beneath the sealing surfaces of the valve. Suitably, the flow through the column is stopped before this step and resumed after it. In these embodiments it is advantageous if the column resin valve has been equilibrated with sanitization solution before the closing/opening.

In some embodiments, before step b), the column with the packed bed of separation resin may be used for separation of a biopharmaceutical. Additionally, or alternatively, after step e), the column with the packed bed of separation resin is used for separation of a biopharmaceutical. The biopharmaceutical may e.g. be an immunoglobulin such as a monoclonal antibody but it can also be a recombinant protein or e.g. a vaccine antigen. In a variant of these embodiments, before step b), the column with the packed bed of separation resin may be used for separation of a first biopharmaceutical and, after step e), the column with the packed bed of separation resin may be used for separation of a second biopharmaceutical which is different from the first biopharmaceutical. The first and second biopharmaceuticals may e.g. be two different monoclonal antibodies.

EXAMPLES

A predefined sanitization method based on peracetic acid (PAA) as sanitization agent was evaluated in an AxiChrom™ 300 column (GE Healthcare) packed with agarose beads, as used in the MabSelect™ SuRe Protein A resin (GE Healthcare), by triplicate studies using *P. aeruginosa* as challenging organism. All parts in contact with the process flow including the resin were pre-cleaned, challenged, sanitized and evaluated. Microbial sampling was performed at predetermined sites on the system. Flow through samples were collected from the process chamber during the run and from the flush channel, process chamber and resin valve after finishing the sanitization method. Additional flow through samples were collected after five to six days of clean hold. Test methods used are presented below. The results were evaluated against stated acceptance criteria.

Tested Item:
AxiChrom 300/300 column, serial no. 28976588, 300 mm diameter acrylic tube, stainless steel bed supports.
Study 1: 10 µm net in top and bottom bed supports
Study 2 and 3: 10 µm net in bottom bed support and 20 µm net in top bed support with 273*2.62 mm EPDM O-ring (art. no. 29-1659-36)

All O-rings in contact with the process stream and directly or indirectly connected to a sampling point were replaced with new ones. The new O-rings were used in all 3 experimental studies.

Sampled Hardware Parts:
See Table 1 and FIGS. 4-10.

Challenging Organism(s):
*Pseudomonas aeruginosa*, ATCC 9027, Gram negative bacteria Concentration of Challenging Organism:
$1 \times 10^7$ CFU/ml or CFU/unit (CFU=Colony forming unit)

Sanitization Agent:
Peracetic acid, 20 mM aqueous solution through the packed bed and in the valves. 100 mM in the flush channel.

Resin:
Highly crosslinked spherical agarose beads of 85 µm volume-weighted median diameter (d50,v), sieved between 40 and 130 µm sieving cloths.

Preparation of System and Column
As a pre-cleaning process all column parts that could be disassembled (column lid, tube, bottom, and adapter backing plate excluded) were soaked in 1 M NaOH-solution for 24 hours, then rinsed with sterile purified water before assembling.

The rest of the column, i.e. column lid, bottom and the adapter backing plate was sprayed with 70% ethanol, while the column tube was wiped with 20% ethanol before assembling.

Before soaking the column parts in 1 M NaOH for 24 hours, all parts used in study 2 and 3 were scrubbed or wiped with a 2% detergent solution (YES), except for small parts such as screws and nuts. The stainless-steel bed supports were cleaned in an ultrasonic bath with 1 M NaOH for 2*15 min at 40° C.

In study 3 the PTFE. thread seal tape on all screws including the fasteners for bed supports were replaced and then autoclaved for 30 min at 121° C.

When possible due to their size, the column parts were assembled in a LAF-hood. During assembly the parts were sprayed with 70% ethanol. This ethanol was replaced in study 2 and 3 with Klercide™ 70/30 Denatured Ethanol.

Also, the ÄKTA™ process skid (GE Healthcare) was pre-cleaned by first flushing it with 20 mM PAA and then filling with 1 M NaOH and left overnight.

Packing of the AxiChrom 300 Column with Resin

To prepare the column for packing, the column was purged from air by pumping purified water up flow until the column tube was filled. The adapter was in its priming position during this procedure. Hereafter a flow was applied upwards through the column and a diaphragm valve in the flow path after the column was manually adjusted to achieve a pressure of 0.3 bar. The adapter was then taken down at 40 cm/h with the flow still on and leaving the flush channels open until the adapter had passed the priming groove in the tube. The adapter was stopped at about 40 cm (study 3) height and the column tube were then filled with 1 M NaOH and stored overnight. After this the column was equilibrated with purified water and the adapter was moved down to starting position, 1 cm from bottom bed support.

The column was then packed with the resin using 50 mM NaCl as packing solution inoculated with the challenging organism. The packing was performed manually using the AxiChrom Master control unit. The homogenous slurry of the infected resin was drawn into the column by raising the adapter, initially at 300 cm/h and at the end around 100 cm/h since all the resin was chased into the column. The chasing was done by pouring 50 mM NaCl (study 1 and 3) or 20 mM PAA (study2) into the slurry tank while the adapter was still moving upwards in the column. The resin valve was then closed, and the valve and tubing were rinsed free from resin using 20 mM PAA.

The packing was started with the bottom mobile phase open while the adapter was driven downwards at 60 cm/h to a target bed height of 10 cm, but the actual bed heights were between 9.7-10.2 cm. The actual bed height was determined by the bed height that was achieved when the resin had been packed in purified water in an AxiChrom 300/500 column with Intelligent packing prior to the packing in the Hygienic lab. A CIP with 1 M NaOH had been performed of the beds packed in the AxiChrom 300/500 and then unpacked in sterile filtered 50 mM NaCl and this slurry was then packed in the Hygienic lab as described above.

Preparation for Infection of Resin

TSA plates streaked with *P. aeruginosa* ATCC 9027 (in-house glycerol stocks) were incubated in 37° C. over night (O.N.). Fresh colonies from those plates were transferred to 200 mL of TSB-media and left shaking in 37° C. O.N. Based on measured optical densities (ODs) of the inoculates and the assumption that 1 OD≈$2\times10^9$ CFU/mL for *P. aeruginosa*, calculations were made on the volumes needed of the inoculate to be added to the resin slurry suspended in 50 mM NaCl. The aim was to reach the final concentrations of approximately ~$10^7$ CFU/ml in the challenging organism suspensions. The microorganism concentrations were determined with test method 5.

Sanitization Procedure

Study 1:

The resin was packed to bed height 9.7 cm. The sanitization study started with rinsing the packed bed with sterile purified water, 2 column volumes (CV), down-flow, at 60 cm/h, followed by 20 mM PAA down-flow, at 120 cm/h for 4 min. The adapter was moved upwards at 120 cm/h to 14 cm while 20 mM PAA was pushed through the bed downflow at 150 cm/h. The flow was stopped, and adapter moved downwards to 9.7 cm at 60 cm/h pushing excess liquid out through the bottom mobile phase. Finalized the PAA treatment by running a downflow with 20 mM PAA at 300 cm/h. The flow was then stopped and the PAA treated bed was then incubated for 15 min before equilibration with purified water was started by running a downflow at 300 cm/h for 2 CV.

During this first sanitization study liquid samples were collected at: the consolidation phase of the packing, then at the rinse with 2 CV of water after packing and finally after equilibration with 2 CV of purified water at the end of the method.

Study 2:

Before the column was packed the flush channel (the area between the upper and lower scraper seals) was filled with 100 mM PAA using a syringe and then the resin was packed to bed height 10.2 cm. The sanitization study started with rinsing the packed bed with sterile purified water, 2 CV, down-flow, at 60 cm/h, followed by 20 mM PAA down-flow, at 120 cm/h for 4 min. The adapter was moved upwards at 120 cm/h to 14.5 cm while 20 mM PAA was pushed through the bed downflow at 150 cm/h. The flow was stopped, and the adapter moved downwards to 10.2 cm at 60 cm/h pushing excess liquid out through the bottom mobile phase outlet/inlet. The adapter movement was repeated by running 20 mM PAA down-flow, at 120 cm/h for 4 min. The adapter was moved upwards at 120 cm/h to 14.5 cm while 20 mM PAA was pushed through the bed downflow at 150 cm/h. The flow was stopped, and the adapter moved downwards to 10.2 cm at 60 cm/h pushing excess liquid out through the bottom mobile phase outlet/inlet.

The PAA treatment was finalized by running a downflow with 20 mM PAA at 300 cm/h for 2 CV. The flow was stopped and the PAA treated bed was then incubated for 5 min before equilibration with purified water was started by running a downflow at 300 cm/h for 2 CV.

During the second sanitization study liquid samples were collected at: the consolidation phase of the packing, then at the rinse with 2 CV of water after packing and finally after equilibration with 2 CV of purified water at the end of the method. After the sanitization method the packed bed and resin valve was equilibrated with 20% ethanol and liquid samples were collected after 2 CV for the packed bed and 5 L for the resin valve. The 100 mM PAA in the flush channel was rinsed out with 20% ethanol until pH increased and then a liquid sample was collected.

The column was then left in the Hygienic lab with the storage solution (20% ethanol) for a 5 day "clean hold" while connected to the ÄKTAprocess skid. After this a liquid sample of the ethanol in the resin valve was collected and then 20% ethanol was run downflow at 60 cm/h through the packed bed and liquid samples were collected after 0.6 CV and 1.2 CV. The liquid in the flush channel was also collected.

Study 3:

Before the column was packed, the flush channel (the area between the upper and lower scraper seals) was filled with 100 mM PAA using a syringe and then the resin was packed to bed height 10.1 cm. The sanitization study started with rinsing the packed bed with sterile purified water, 2 CV, down-flow, at 60 cm/h, followed by 20 mM PAA down-flow, at 120 cm/h for 4 min. The adapter was moved upwards at 120 cm/h to 14.4 cm while 20 mM PAA was pushed through the bed downflow at 170 cm/h. The flow was stopped, and adapter moved downwards to 10.1 cm at 60 cm/h pushing excess liquid out through the bottom mobile phase outlet/inlet. The adapter movement was repeated by running 20 mM PAA down-flow, at 120 cm/h for 4 min (PAA~3 cm into the packed bed). The flow was stopped, and the resin valve piston was open and closed twice within 6 s. The adapter was moved upwards at 120 cm/h to 14.4 cm while 20 mM PAA was pushed through the bed downflow at 170 cm/h. The flow was stopped, and adapter moved downwards to 10.1 cm at 60 cm/h pushing excess liquid out through the bottom mobile phase outlet/inlet.

The PAA treatment was finalized by running a downflow with 20 mM PAA at 300 cm/h for 2 CV. The flow was then stopped and the PAA treated bed was then incubated for 5 minutes before equilibration with purified water was started by running a downflow at 300 cm/h for 2 CV.

During the third sanitization study liquid samples were collected at: the consolidation phase of the packing, then at the rinse with 2 CV of water after packing and finally after equilibration with 2 CV of purified water at the end of the method. After the sanitization method the packed bed and resin valve was equilibrated with 20% ethanol and liquid samples were collected after 2 CV for the packed bed and 3 L for the resin valve. The 100 mM PAA in the flush channel was rinsed out with ~150 ml 20% ethanol until pH increased and then a liquid sample was collected.

The column was then incubated in the Hygienic lab with the storage solution (20% ethanol) for a 6 day "clean hold" while connected to the ÄKTAprocess system. Before any liquid samples were collected after the "clean hold" the system was flushed with 20 mM PAA and then equilibrated with 20% ethanol to minimize the risk of contaminants from the ÄKTAprocess system. A liquid sample of the ethanol in the resin valve was collected and then 20% ethanol was run downflow at 60 cm/h through the packed bed and liquid samples were collected after 0.6 CV and 1.2 CV. A liquid sample of the filtered 20% ethanol was also collected from the top mobile phase inlet/outlet as a control. The liquid in the flush channel was also collected.

Microbial Sampling

Samples were taken at predetermined sites.

Disassembling the Column for Microbiological Sampling

When all liquid samples had been collected the sampling of the different columns parts began. Sampling points are described in Table 1 and FIGS. 4-10. Before the disassembly started excess liquid was drained from the packed bed through the bottom mobile phase outlet/inlet. The column was then moved to a position in the Hygienic lab where the top unit of the column could be fixated with slings to a sturdy fixation in the celling. Then the upper hinge was loosened, and the bottom flange bolts were removed and when the adapter was moved down at 100-200 cm/h it enabled sampling of the packed bed. This disassembly method made it possible to get an opening of ~8 cm through which most of the resin was then removed with plastic spoons. Several more of the predetermined sites could then be sampled. The adapter was then moved back to the starting position (the height of the packed bed) and the bottom flange bolts and upper hinge was put back. The column was then disassembled in the normal way using the Maintenance wizard in the AxiChrom Master. Once the column tube was in the swing out position smaller parts that had to be sampled e.g. bed supports or top inlet these were removed, and sampling was performed in the LAF-hood.

Most of the sampling took place in the LAF in the Hygienic lab. The remaining parts was sampled outside the LAF in the Hygienic lab. System parts were handled in the most aseptic way possible. All solutions used in the sanitization process were also analyzed.

Microbial sampling was performed by one of the following methods:

Test Method 1, Microbial Air Sampling

Sampling of air for airborne microorganisms was conducted with a Microbial Air Sampler (MAS). A MAS loaded with an agar plate is positioned at a suitable measuring point. When the measuring starts, a pre-defined volume of surrounding air is passed through the machine. Microorganisms will be collected on the agar surface by impaction.

Test Method 2, Direct Filtration

Sample solutions (minimum 10 mL) were collected in sterile tubes and then filtered through a 0.45 μm cellulose nitrate membrane filters. Filters were incubated on agar plates at 30-35° C. for 5 days after which the plates were inspected for CFUs.

Test Method 3, Swab

Surface samples were taken with swabs. The swab was inserted into the tube containing the isotonic swab rinse solution and vortexed for a minimum of 20 s. The solutions including the swabs were poured into Petri dishes and mixed with 30 mL of temperature controlled molten agar. Maximum temperature of the molten agar should be 45° C. After solidification, plates were incubated at 30-35° C. for 5 days after which the plates were inspected for CFUs.

Test Method 4, Peptone Water Filtration

Detachable parts were aseptically removed and transferred to a sterile tube subsequently filled with 50 mL of sterile peptone water and then vigorously shaken at 280 rpm for at least 20 min in room temperature (RT). The solutions were filtered through a 0.45 μm cellulose nitrate membrane filter. Filters were incubated on agar plates at 30-35° C. for 5 days after which the plates were inspected for CFUs.

Test Method 5, Viable Count

Samples of challenging organism suspensions were diluted in series in 0.9% NaCl. Samples from the diluted suspensions were plated on agar plates and incubated at 30-35° C. for 1-2 days after which the plates were inspected for CFUs. The concentration of challenging organism was determined in the sampled suspensions.

Test Method 6, Agar Plate

A sample of the chromatography resin was taken after sanitization and mixed with 30 ml of molten agar.

One gram of resin was aseptically transferred into a sterile container. The molten agar was aseptically added to the container and mixed with the resin to become homogenously suspended. Maximum temperature of the molten agar should be 45° C. The suspension was transferred to and allowed to solidify in Petri dishes. The plates were incubated at 30-35° C. for 5 days after which the plates were inspected for CFUs.

Criteria for Acceptance

Challenging organism concentration should be higher than $10^6$ CFU/mL in the suspended resin solution applied.

Liquid samples (L-T) taken after finishing the sanitization procedure, clean hold of 5-6 days included, shall have a maximum concentration of 10 CFU/10 mL of contaminating organisms, including the challenging organism. Results from samples taken on the hardware in study 2 and 3 will not be taken into account.

If liquid samples (L-T) are negative (0 CFU/10 mL), a maximum of 10% of samples taken on the hardware in study 2 and 3, i.e. 5 samples, are allowed to be contaminated with organisms, including the challenging organisms.

Results

Table 1 presents the results from sanitization studies 1 to 3 including sample points, liquid samples and control samples. Discovered contaminations are presented by name in the first column in the table. Sample points have been denoted with a letter or figure and presented visually in FIGS. 4-10.

TABLE 1

Results

| Organisms | Sampling point | Sample | Test number no. | Unit method | Result study 1 | Result study 2 | Result study 3 |
|---|---|---|---|---|---|---|---|
| | Resin suspension in sterile filtered 50 mM NaCl without challenging organism | A | 2 | CFU/decanted volume | 0 | TNTC* | 0 |
| | Solution in flush channel, 100 mM PAA before application | B | 2 | CFU/50 mL | N/A | 0 | 0 |
| | Resin suspension with challenging organism before application | C | 5 | CFU/mL | $13.2 \times 10^7$ | $10.8 \times 10^6$ | $9.0 \times 10^6$ |
| | Chasing of resin suspension, 50 mM NaCl before application | D | 2 | CFU/50 mL | N/A | N/A | 0 |
| Challenging organism | Consolidation, effluent from start | E | 5 | CFU/mL | $9.7 \times 10^7$ | N/A | N/A |
| Challenging organism | Consolidation, effluent after 50% of consolidation | F | 5 | CFU/mL | $11.8 \times 10^7$ | N/A | N/A |
| Challenging organism | Consolidation, effluent when finished | G | 5 | CFU/mL | $10.4 \times 10^7$ | 0 | $9.7 \times 10^6$ |
| Sphingomonas paucimobilis and Pseudomonas aeruginosa | Rinse of consolidated resin, purified water (PW) before application and sterile filtration | H | 2 | CFU/50 mL | 2 | N/A | N/A |
| Unidentified cocci-shaped organism | Rinse of consolidated resin, sterile filtered PW, before application | I | 2 | CFU/50 mL | 1 | 0 | 0 |
| Challenging organism | Rinse of consolidated resin, sterile filtered PW, flowthrough after 1.9 column volumes (CV) | J | 5 | CFU/mL | TNTC* | 0 | $2.0 \times 10^4$ |
| | Sanitization solution, 20 mM PAA, before application | K | 2 | CFU/50 mL | 0 | 0 | 0 |
| Pseudomonas aeruginosa | Rinse after applied sanitization solution, sterile filtered PW, flowthrough after 2 CV | L | 2 | CFU/50 mL | 11 | 0 | 0 |
| | Rinse/equilibration of resin, sterile filtered 20% EtOH, flowthrough after 2 CV, Day 0 | M | 2 | CFU/50 mL | N/A | 0 | 0 |
| | Rinse/equilibration of resin valve, sterile filtered 20% EtOH, flowthrough after 2 CV, Day 0 | N | 2 | CFU/50 mL | N/A | 0 | 0 |
| | Flush channel in adapter, 100 mM PAA, push out of PAA with sterile filtered 20% EtOH, Day 0 | O | 2 | CFU/50 mL | N/A | 0 | 0 |
| | Clean hold, sterile filtered 20% EtOH, before application, Day 5-6 | P | 2 | CFU/50 mL | N/A | 0 | 0 |
| | Flowthrough after 0.6 CV rinse/equilibration with 20% EtOH, Day 5-6 | Q | 2 | CFU/50 mL | N/A | 0 | 0 |
| | Flowthrough after 1.2 CV rinse/equilibration with 20% EtOH, Day 5-6 | R | 2 | CFU/50 mL | N/A | 0 | 0 |
| Corynebacterium afermentans | Flowthrough of resin valve in bottom inlet, 20% EtOH; Day 5-6 | S | 2 | CFU/50 mL | N/A | 1 | 0 |
| Micrococcus luteus/lylae and Gram-positive cocci | Liquid from flush channel in adapter, 20% EtOH, Day 5-6 | T | 2 | CFU/50 mL | N/A | 0 | 2 |
| Air | Microbial air sample on TSA-agar next to LAF hood | U | 1 | CFU/m$^3$ | 7 | 59 | 42 |
| Micrococcus luteus/lylae | Bottom surface 42 of column tube 6 | 1 | 3 | CFU/unit | 0 | 1 | 0 |
| | O-ring 44 in bottom bed support, facing end of tube 6 | 2 | 3 | CFU/unit | 0 | 0 | 0 |
| Micrococcus luteus/lylae | Resin | 3 | 6 | CFU/g | 0 | 0 | 1 |
| Micrococcus luteus/lylae | Resin from deadleg 102 | 4 | 6 | CFU/g | 0 | 2 | 0 |
| | Outer perimeter 104 of bottom bed support 10 | 5 | 3 | CFU/unit | 0 | 0 | 0 |

TABLE 1-continued

Results

| Organisms | Sampling point | Sample | Test number no. | Unit method | Result study 1 | Result study 2 | Result study 3 |
|---|---|---|---|---|---|---|---|
| | Net surface 106 of bottom bed support 10 | 6 | 3 | CFU/unit | 0 | 0 | 0 |
| | Weld 108 around mesh screw 110 on bottom bed support 10 | 7 | 3 | CFU/unit | 0 | 0 | 0 |
| | Mesh screw 110, holes for mesh screw tool | 8 | 3 | CFU/unit | 0 | 0 | 0 |
| | Mesh screw 110 surface between holes and piston 60 | 9 | 3 | CFU/unit | 0 | 0 | 0 |
| | Mesh screw 110, top 62 of piston 60 | 10 | 3 | CFU/unit | 0 | 0 | 0 |
| | Interface between piston 60 and mesh screw 110 | 11 | 3 | CFU/unit | 0 | N/A | 0 |
| *Cronobacter sakazakii, Pseudomonas aeruginosa* | Adapter-O-ring 112 between distributor 136 and upper scraper seal 114 | 12 | 3 | CFU/unit | TNTC | 0 | 0 |
| | Adapter-flush channel | 13 | 3 | CFU/unit | TNTC | 0 | 0 |
| | Lower scraper seal 116, facing tube 6 | 14 | 3 | CFU/unit | 0 | 0 | 0 |
| | Lower scraper seal 116, groove | 15 | 3 | CFU/unit | 0 | 0 | 0 |
| | Adapter-lower O-ring 118 between steel ring and lower scraper seal 116 | 16 | 3 | CFU/unit | 1 | 0 | 0 |
| | Metal edge 120 of top bed support 8 facing tube 6 | 17 | 3 | CFU/unit | 0 | 0 | 0 |
| | Weld 122 on outer perimeter of top bed support 8 | 18 | 3 | CFU/unit | 0 | 0 | 0 |
| | Top bed support 8 net surface 124 facing resin | 19 | 3 | CFU/unit | 0 | 0 | 0 |
| | Weld around mesh screw 50 on top bed support 8 | 20 | 3 | CFU/unit | 0 | 0 | 0 |
| | Top bed support 8 mesh screw 50, all holes | 21 | 3 | CFU/unit | 0 | 0 | 0 |
| | Top bed support 8 mesh screw 50 surface | 22 | 3 | CFU/unit | 0 | 0 | 0 |
| Unidentified cocci-shaped organism | Top bed support 8 mesh screw 50 edge | 23 | 3 | CFU/unit | TNTC | 0 | 0 |
| | Top bed support 8 mesh screw 50 O-ring 52 | 24 | 4 | CFU/unit | 0 | N/A | N/A |
| Unidentified cocci-shaped organism | Top bed support 8 mesh screw 50 O-ring groove | 25 | 3 | CFU/unit | TNTC | N/A | N/A |
| | Adapter-top of "spaghetti" O-ring 126 | 26 | 3 | CFU/unit | N/A | 0 | 0 |
| Gram positive rod (study 2), *Micrococcus luteus/lylae* (study 3) | Surface 128 of bed support ring facing adapter plate | 27 | 3 | CFU/unit | N/A | TNTC | 1 |
| | Adapter-outer perimeter O-ring 112 facing scraper seal 114 | 28 | 3 | CFU/unit | 0 | 0 | 0 |
| *Bacillus clausii* | Adapter-"spaghetti" O-ring 126 groove | 29 | 3 | CFU/unit | N/A | TNTC | 0 |
| | Adapter-outer perimeter O-ring 118 groove horizontal surface | 30 | 3 | CFU/unit | 0 | 0 | 0 |
| | Adapter-outer perimeter O-ring 118 groove vertical surface | 31 | 3 | CFU/unit | 0 | 0 | 0 |
| Same morphology as challenging organism | Adapter-outer bed support steel ring 134, inclined surface 130 facing O-ring 132 | 32 | 3 | CFU/unit | TNTC | 0 | 0 |
| Same morphology as challenging organism | Adapter-interface between outer bed support steel ring 134 and net 8 | 33 | 3 | CFU/unit | TNTC | 0 | 0 |
| | Adapter-net 8, surface facing distributor 136 | 34 | 3 | CFU/unit | 0 | 0 | 0 |

TABLE 1-continued

Results

| Organisms | Sampling point | Sample | Test number no. | Unit method | Result study 1 | Result study 2 | Result study 3 |
|---|---|---|---|---|---|---|---|
| | Adapter-inner bed support steel ring 138, interface between vertical surface and net 8 | 35 | 3 | CFU/unit | 0 | 0 | 0 |
| Same morphology as challenging organism | Adapter-inner bed support steel ring 138, O-ring 52 | 36 | 3 | CFU/unit | 2 | 0 | 0 |
| Same morphology as challenging organism | Adapter-inner bed support steel ring 138, O-ring 52 groove | 37 | 3 | CFU/unit | TNTC | N/A | N/A |
| Same morphology as challenging organism | Adapter-surface of upper O-ring 112 groove | 38 | 3 | CFU/unit | TNTC | 0 | 0 |
| | Adapter distributor 136, on top of grooves | 39 | 3 | CFU/unit | 0 | N/A | N/A |
| | Adapter distributor 136 surface between grooves | 40 | 3 | CFU/unit | 0 | N/A | N/A |
| | Adapter distributor 136, six holes | 41 | 3 | CFU/unit | 0 | N/A | N/A |
| *Micrococcus luteus/lylae* | Adapter-distributor hole 140, vertical surface facing O-ring 52 | 42 | 3 | CFU/unit | 0 | 1 | 0 |
| | Top valve 16-O-ring 142 between top inlet and TC connector 54 | 43 | 4 | CFU/unit | 0 | N/A | N/A |
| | Top valve 16-O-ring 142 groove between top inlet and TC connector 54 | 44 | 3 | CFU/unit | 0 | N/A | N/A |
| | Top valve 16-O-ring 58 oval | 45 | 3 | CFU/unit | 0 | 0 | 0 |
| | Top valve 16-chamber 56 | 46 | 3 | CFU/unit | N/A | 0 | 0 |
| | Bottom bed support 106-outer O-ring 44 facing edge of tube 6 | 47 | 3 | CFU/unit | 0 | N/A | N/A |
| Same morphology as challenging organism | Bottom bed support-O-ring 64 in interface between mesh screw 110 and piston 60 | 48 | 3 | CFU/unit | TNTC | 0 | 0 |
| | Bottom bed support-mesh screw 110 edge | 49 | 3 | CFU/unit | 0 | 0 | 0 |
| *Cronobacter sakazakii, Sphingomonas paucimobilis* | Bottom bed support 106-O-ring 64 facing mesh screw 110 | 50 | 4 | CFU/unit | 3 | N/A | N/A |
| | Bottom bed support-inner steel ring 144 inclined surface with O-ring groove facing mesh screw 110 | 51 | 3 | CFU/unit | 0 | N/A | N/A |
| Unidentified organism | Bottom bed support-top of O-ring 46 facing steel ring 148 | 52 | 3 | CFU/unit | TNTC | 0 | 0 |
| | Bottom bed support-distributor 146, on top of grooves | 53 | 3 | CFU/unit | 0 | N/A | N/A |
| | Bottom bed support-surface between distributor 146 grooves | 54 | 3 | CFU/unit | 0 | N/A | N/A |
| | Bottom bed support 10-distributor 146, six holes | 55 | 3 | CFU/unit | 0 | N/A | N/A |
| Unidentified organism | Bottom bed support-distributor 146, vertical surface facing inner bed support steel ring with O-ring | 56 | 3 | CFU/unit | TNTC | N/A | N/A |
| Unidentified organism | Bottom bed support-outer steel ring 148, inclined surface facing bottom adapter O-ring 46 | 57 | 3 | CFU/unit | TNTC | N/A | N/A |
| Unidentified organism | Bottom bed support-interface between outer steel ring 148 and net 10 | 58 | 3 | CFU/unit | TNTC | 0 | 0 |

TABLE 1-continued

Results

| Organisms | Sampling point | Sample | Test number no. | Unit method | Result study 1 | Result study 2 | Result study 3 |
|---|---|---|---|---|---|---|---|
| | Bottom bed support-net 10 surface | 59 | 3 | CFU/unit | 0 | 0 | 0 |
| | Bottom bed support-inner steel ring 144, interface between vertical surface and net 10 | 60 | 3 | CFU/unit | 0 | 0 | 0 |
| Unidentified cocci-shaped | Bottom bed suppor-inner steel ring 144, O-ring organism | 61 | 3 | CFU/unit | 7 | 0 | 0 |
| | Bottom bed support-inner steel ring 144, O-ring groove | 62 | 3 | CFU/unit | 0 | N/A | N/A |
| Unidentified organism | Bottom valve 30-O-ring 150 and piston 60 surface facing each other | 63 | 3 | CFU/unit | TNTC | 0 | 0 |
| Unidentified cocci-shaped organism | Bottom valve-outer O-ring 152, facing adapter | 64 | 4 | CFU/unit | 4 | N/A | N/A |
| Unidentified organism | Bottom valve 30-inner O-ring 154, facing adapter | 65 | 4 | CFU/unit | 13 | N/A | N/A |
| Unidentified organism | Bottom valve 30-O-ring, resin inlet 26 of bottom valve | 66 | 4 | CFU/unit | 1 | N/A | N/A |
| | Bottom valve 30-O-ring, mobile phase inlet 18 of bottom valve | 67 | 4 | CFU/unit | 0 | N/A | N/A |
| | Bottom valve 30-rinse inlet 156 spray part | 68 | 3 | CFU/unit | 0 | N/A | N/A |
| | Bottom valve 30-rinse inlet 156, O-ring | 69 | 4 | CFU/unit | 0 | N/A | N/A |
| | Bottom valve 30-compartment 158 between outer 152 and inner 154 O-ring | 70 | 3 | CFU/unit | N/A | 0 | 0 |
| | Bottom valve 30-inside resin chamber 160 | 71 | 3 | CFU/unit | N/A | 0 | 0 |
| | Bottom valve 30-oval shape O-ring 162 inside valve | 72 | 3 | CFU/unit | 0 | 0 | 0 |
| Same morphology as challenging organism | Bottom valve 30-FEP O-ring 164, inside valve | 73 | 3 | CFU/unit | TNTC | 0 | 0 |
| | Negative control-sterile 0.9% NaCl solution | 74 | 2 | CFU/50 mL | 0 | 0 | 0 |
| | Positive control-swab dipped into inoculum | 75 | 3 | CFU/unit | TNTC | TNTC | TNTC |
| | Negative control-swab directly transferred to isotonic solution | 76 | 3 | CFU/unit | 0 | 0 | 0 |
| | Positive control-miniswab dipped into inoculum | 77 | 3 | CFU/unit | TNTC | TNTC | TNTC |
| | Negative control-miniswab directly transferred to isotonic solution | 78 | 3 | CFU/unit | 0 | 0 | 0 |
| | Positive contro-a swab dipped into inoculum and transferred to peptone water | 79 | 4 | CFU/50 mL | TNTC | N/A | N/A |
| Same morphology as challenging organism | Negative control-peptone water, added directly onto filter | 80 | 4 | CFU/50 mL | TNTC | N/A | N/A |
| | Positive control-TSA plates w resin suspension w challenging organism before application | 81 | N/A | CFU/unit | 128/136 | 117/99 | 98/82 |
| | Negative control-TSA plate directly bagged without opening the lid | 82 | N/A | CFU/unit | 0 | 0 | 0 |

*TNTC = Too numerous to count

Design Discussion

Before the sanitization study started one specific part of the movable adapter design was thought to probably be more difficult to clean. This is the dead leg that is formed between the top bed support and column tube. This design risk is general for process columns with a movable adapter.

An important feature of this sanitization study is that first the homogenous resin slurry was inoculated with the challenging organism and then packed in the column. This ensured that all critical parts of the column were challenged with a high concentration of P.a. In simpler studies the challenging organisms were applied through the mobile phase after the column had been packed, hence it is unclear if e.g. the dead leg was properly challenged.

Sanitization Study

Three sanitization studies were conducted. Only the last study was considered to be complete and approved against stated acceptance criteria. The first study did not meet all the criteria. The second study lacked a control sample with the purpose to show that the column had been correctly challenged. This sample, denoted Gin Table 1, showed that the Column was challenged with 0 CFU/mL instead of an expected value in the range $10^6$ to $10^7$. The most likely cause for this result is the usage of PAA during chasing of the last resin into the column and that this led to a reduction of the concentration of the challenging organism to a level that could not be detected.

The concentration of the challenging organism in the prepared pre-contaminated resin suspension was in the expected range of $10^6$ to $10^8$ CFU/mL. The positive control taken after finished consolidation (sample G in Table 1) was in the same range as before application of the resin in study 1 and 3. As mentioned before, the corresponding sample in study 2 showed 0 CFU/mL, probably due to the chasing with 20 mM PAA.

The rinse with 1.9 CV of sterile water (sample J in Table 1) showed a good reductive effect of log 3 on the concentration of the challenging organism.

Contaminations were found on many places in study 1. In sample point 16, representing the surface of the lower O-ring between bed support steel ring and lower scraper seal, a contamination was found having the same morphology as the challenging organism. This sample point is in contact with the process stream. The challenging organism together with other organisms were also found on other spots. Study 1 did not meet the acceptance criteria.

Contaminations were found at four sample point in study 2, none of them was the challenging organism and none of them in contact with the process stream. The study did meet the acceptance criteria but since the positive control (sample G in Table 1) did not show the challenging organism, this study cannot be used to prove that the column and resin can be sanitized.

In study 3, no challenging organism was discovered. Only two other contaminations not in contact with the process stream were found (sample 3 and 27 in Table 1). The contamination in sample 3, situated in the resin, were *Micrococcus luteus/lylae*, which are gram-positive cocci common on the human skin. The sample was taken and handled partly outside a LAF, which was necessary for this sample. The sample posed a higher risk to be contaminated for this reason. The contamination in sample 27, the same organisms as in sample 3, was found on the top of the outer steel ring. It is difficult to find a cause for this, but the most likely reason can be the handling by the operator. This study, however, met the acceptance criteria and was therefore approved.

Air samples taken in all three studies showed normal levels of airborne microbial burden between 7 to 59 CFU/m$^3$ in the hygienic lab. This indicate that the experimental procedures were carried out at a good level when it comes to hygienic and aseptic practices and that the risk of contamination of the samples by the airborne organisms was low.

Control samples 74 to 82 in Table 1 indicated that materials and procedures did not pose a risk of compromising the studies.

During the entire study the sanitization method was refined between the different runs. The microbiological sampling results from study 1 indicated that the method needed to be revised since the challenging organism was found in areas related to the resin valve, flush channel and dead leg between adapter and column tube.

Prior to the second study some additional experiments were performed by packing an AxiChrom 300 column with resin mixed with riboflavin. The result from this experiment led to the conclusion that dual adapter strokes during the PAA treatment could increase the chance of liquids being exchanged in the dead leg between adapter and column tube.

The issue with the resin valve was most likely due to that the challenging organisms got stuck between the piston and sealing O-ring. When the piston closed at the end of the filling some of the inoculated slurry got stuck and therefore could not be cleared although the rest of the resin valve was rinsed and filled with 20 mM PAA.

The issue with contaminants associated with the flush channel could be due to the fact the study was performed in a column with an old column tube. If there are minor scratches in the acrylic tube there is a small risk that liquid from the process chamber could to pass into the flush channel especially while the adapter is moving.

These conclusions led to three major changes in the method that was used in study 2.

First, the slurry was chased with 20 mM PAA at the end of the filling of the column to avoid getting the challenging organism trap between the piston and sealing O-ring. Furthermore, the flush channel was filled with 100 mM PAA, which should kill most contaminants almost instantly. The method was also altered to include dual strokes with the adapter during the PAA treatment of the bed.

In the last study, run 3, the major change compared to the second study was that chasing of the slurry during filling was done with 50 mM NaCl instead of PAA. The potential problem of trapping contaminants between the piston and the sealing O-ring in the resin valve was solved by opening and closing the resin valve piston twice during the second stroke of the adapter. At this step there would be 20 mM PAA on both sides of the piston and its O-ring and once it opens any trapped contaminants will be subjected to 20 mM PAA.

These iterations of the method eventually lead to the successful result of study 3.

Method Considerations/Improvements

The sanitization studies described in this report focused primarily on the development of a method that could sanitize e.g. MabSelect/MabSelect SuRe in an AxiChrom column or other column with movable adapter. Stability of the packed bed after running the sanitization method is also an important factor. The fact that the adapter is lifted and packed into the bed several times might affect the bed integrity to some extent. If this is an issue, a remedy can be to fluidize the bed inside the column and then pack it to the initial bed height. Different resins have been evaluated using the fluidization technique with very promising results and the beds were proven to be stable. Based on this information the recommendation would be to after the bed has been sanitized and equilibrated with PW, fill the flush channel with 100 mM PAA and then move the adapter upwards and perform a fluidization inside the column followed by consolidation and compression for repacking. The compression can suitably be increased with up to 0.04%, such as 0.02-0.03%, compared with the compression before sanitization, to fully restore column efficiency.

Figure 12:
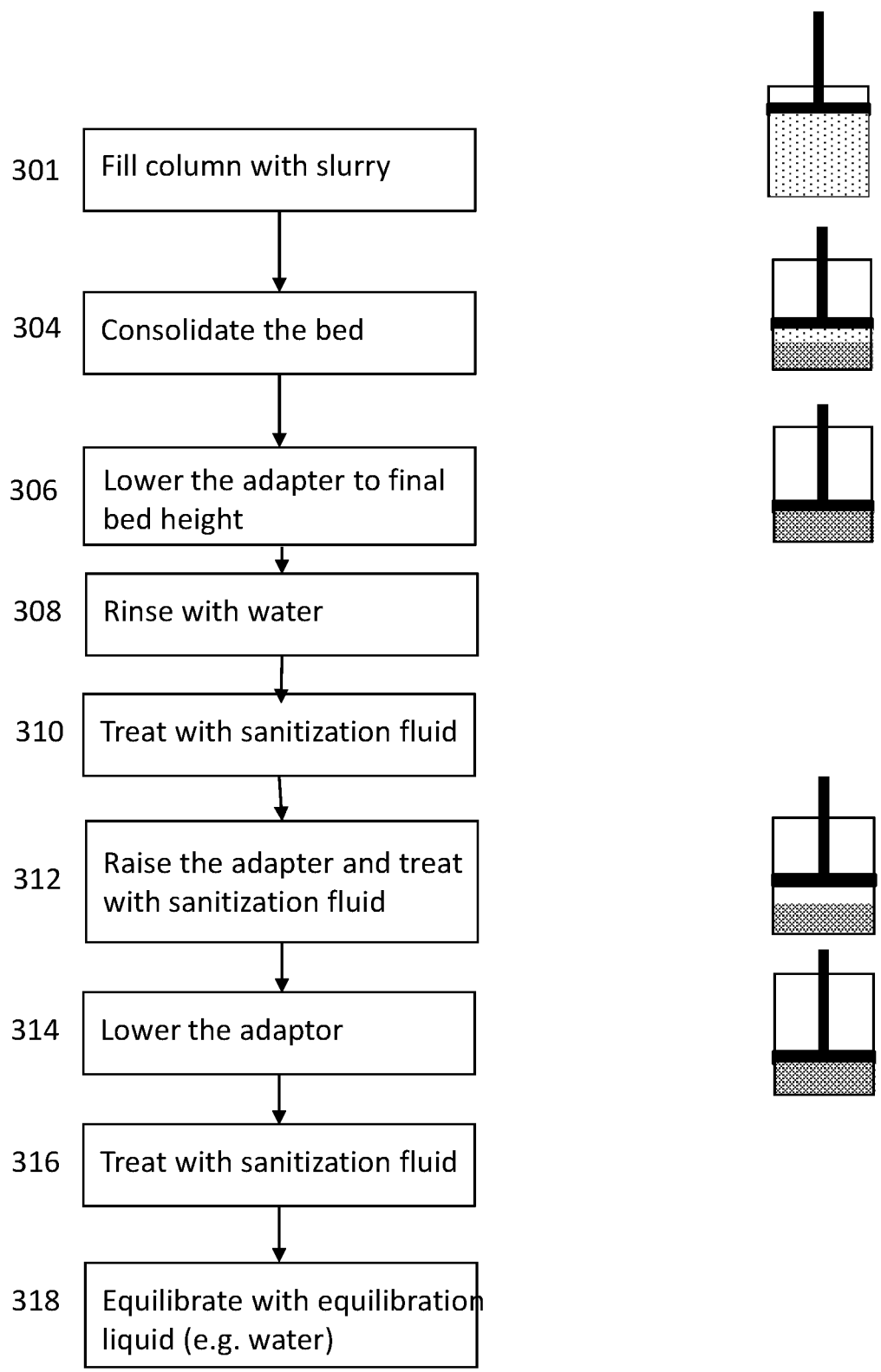
FIG. 12 shows a schematic view of a combined packing and sanitization process.

A schematic picture of the method used in the last study can be seen in FIG. 12. For a more general description of the method see FIG. 11.

The illustration of the method shows that it starts with a packed bed in step 202, hence the method can be used both when packing new resin for the first time or for columns already in production. During the development of the sanitization method there was not enough time to fully optimize all the steps of the methods. By increasing the velocities, the contact time with PAA could probably be decreased, but remember that higher bed heights might not withstand very high flow velocities. A few suggestions of optimization at different steps could be:

In step 308, rinse with water at a flow velocity close to maximum specified for the resin.

In step 310, increase flow velocity and/or decrease the time/distance that PAA is pushed into the packed bed.

In step 312, raise the adapter at a velocity lower than the flow velocity used in step 310 and 312. The distance by which the adapter is lifted could also probably be lowered.

In step 314, lower the adapter to the same bed height as in step 308, faster but still slow enough that the resin in the dead leg has time to fall by gravity. If the adapter distance is decreased in step 312, the adapter velocity in step 314 might need to alter as well.

In step 316, preferably use the same velocity as for step 310. When this step is performed, PAA should preferably be pushed through the entire bed.

In step 208, make sure the flow is stopped, then open and close the resin valve. It might be that only open and closing the valve once will be enough to get PAA between the piston and the O-ring that it is sealing against. Alternatively, the step can be repeated at least once.

If step 312 is repeated, preferably use the same velocity as the first instance and make sure the flow velocity is high enough before moving the adapter upwards.

When step 314 is repeated, lower the adapter preferably with the same velocity as in the first instance. The final bed height should probably be different from that of step 306 if one wants to have a stable bed without performing fluidization of the bed after step 318. Since the bed has been subjected to a repeated packing and expansions in the previous steps the beads have probably become more densely packed, hence the bed height in step 314 should be slightly lower than in step 306.

In step 316, adjust flow velocity to get a contact time with PAA that is less than the recommendation (40 min for 20 mM PAA). Remember that higher bed heights tolerate lower velocities and take in account the viscosity for the PAA solution (specification for MabSelect SuRe is 500 cm/h with water at 20 cm bed height).

Between steps 316 and 318, include a pause if the contact time with PAA has been too short when summarizing step 310-316.

In step 318, rinse with water at a flow velocity close to maximum specified for the resin but take in account the viscosity for the PAA solution already in the packed bed.

The sanitization method in study 3 can be used to efficiently sanitize MabSelect SuRe resin, challenged with *P. aeruginosa*, during packing in an AxiChrom 300 column with 10 cm bed height using 20 mM PAA as sanitization agent. The result from the viable count tests (sample C and G, Table 1) together with the result from the sampling (Table 1) shows that the number of challenging organisms and other contaminations have been reduced from pre-determined contamination levels to levels below the ones in the stated acceptance criteria.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties as if individually incorporated.

The invention claimed is:

1. A method for sanitization of a bioprocess chromatography column, comprising the steps of:
   a) providing a bioprocess chromatography column with a packed bed of separation resin particles and a movable adapter;
   b) with the adapter in contact with the packed bed, conveying a sanitization fluid through the packed bed to a column outlet;
   b') closing and opening a column resin valve;
   c) raising the adapter to provide a gap between the packed bed and the adapter;
   d) lowering the adapter to close the gap;
   d') conveying the sanitization fluid through the packed bed to the column outlet; and
   e) conveying an equilibration liquid through the packed bed to a column outlet.

2. The method of claim 1, wherein steps c) and d) are repeated at least once.

3. The method of claim 1, wherein before step b'), said column resin valve has been equilibrated with the sanitization fluid.

4. The method of claim 1, further comprising filling a flush channel between two adapter seals with the sanitization fluid.

5. The method of claim 1, wherein said sanitization fluid comprises an oxidizing agent.

6. The method of claim 5, wherein said oxidizing agent comprises a peracid or hydrogen peroxide.

7. The method of claim 5, wherein said oxidizing agent comprises or is peracetic acid.

8. The method of claim 5, wherein the concentration of the oxidizing agent in said sanitization fluid is 5-100 mM.

9. The method of claim 1, wherein said separation resin comprises a crosslinked polysaccharide.

10. The method of claim 1, wherein proteinaceous affinity ligands are tethered to said separation resin.

11. The method of claim 10, wherein said proteinaceous affinity ligands comprise Protein A or a variant of Protein A.

12. The method of claim 1, wherein said packed bed of separation resin is in contact with said sanitization fluid for 10-50 minutes.

13. The method of claim 1, wherein, before step b), said column with said packed bed of separation resin is used for separation of a biopharmaceutical.

14. The method of claim 1, wherein, after step e), said column with said packed bed of separation resin is used for separation of a biopharmaceutical.

15. The method of claim 1, wherein, before step b), said column with said packed bed of separation resin is used for separation of a first biopharmaceutical and, after step e), said column with said packed bed of separation resin is used for separation of a second biopharmaceutical which is different from said first biopharmaceutical.

16. The method of claim 5, wherein the concentration of the oxidizing agent in said sanitization fluid is 10-30 mM.

17. The method of claim 9, wherein said separation resin comprises crosslinked agarose.

18. The method of claim 1, wherein said packed bed of separation resin is in contact with said sanitization fluid for 20-40 minutes.

\* \* \* \* \*